(12) United States Patent
Sennett et al.

(10) Patent No.: US 9,833,273 B2
(45) Date of Patent: Dec. 5, 2017

(54) CEMENT-DIRECTING ORTHOPEDIC IMPLANTS

(71) Applicant: GLOBUS MEDICAL, INC., Audubon, PA (US)

(72) Inventors: Andrew R. Sennett, Hanover, MA (US); William Harwick Gruber, Southborough, MA (US); Joseph Ernest Richard, Bedford, MA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 0 days.

(21) Appl. No.: 15/433,304

(22) Filed: Feb. 15, 2017

(65) Prior Publication Data

US 2017/0156777 A1   Jun. 8, 2017

Related U.S. Application Data

(63) Continuation of application No. 15/203,843, filed on Jul. 7, 2016, now Pat. No. 9,603,645, which is a continuation of application No. 14/964,613, filed on Dec. 10, 2015, now Pat. No. 9,408,651, which is a continuation of application No. 14/701,577, filed on May 1, 2015, now Pat. No. 9,237,917, which is a continuation of application No. 13/748,139, filed on Jan. 23, 2013, now Pat. No. 9,232,971, which is a continuation of application No. 12/241,979, filed on Sep. 30, 2008, now Pat. No. 8,100,973, which is a continuation of application No. 11/105,783, filed on Apr. 14, 2005, now Pat. No. 7,465,318.

(60) Provisional application No. 60/562,686, filed on Apr. 15, 2004, provisional application No. 60/604,800, filed on Aug. 26, 2004.

(51) Int. Cl.
| | |
|---|---|
| A61F 2/44 | (2006.01) |
| A61B 17/88 | (2006.01) |
| A61F 2/30 | (2006.01) |
| A61F 2/00 | (2006.01) |
| A61B 17/70 | (2006.01) |

(52) U.S. Cl.
CPC ...... *A61B 17/8811* (2013.01); *A61B 17/7098* (2013.01); *A61B 17/8822* (2013.01); *A61B 17/8858* (2013.01); *A61F 2/0063* (2013.01); *A61F 2/30907* (2013.01); *A61F 2/442* (2013.01); *A61F 2/4455* (2013.01); *A61F 2002/3008* (2013.01); *A61F 2002/30019* (2013.01); *A61F 2002/30092* (2013.01); *A61F 2002/30243* (2013.01); *A61F 2002/30912* (2013.01)

(58) Field of Classification Search
None
See application file for complete search history.

(56) References Cited

U.S. PATENT DOCUMENTS 6,740,093 B2 * 5/2004 Hochschuler ...... A61B 17/7097
606/94

* cited by examiner

*Primary Examiner* — Sameh Boles

(57) ABSTRACT

A cement-directing structure for use in cement-injection bone therapy includes a collapsible, self-restoring braided structure with regions of differential permeability to the bone cement. The regions of differential permeability may be provided by areas where the braided mesh density is greater or lesser than surrounding areas and/or by means of a baffle. After the structure is placed in a void within a bony structure, cement is injected into the interior of the structure then oozes out in preferred directions according to the locations of the regions of differential permeability.

20 Claims, 27 Drawing Sheets

CEMENT-DIRECTING ORTHOPEDIC IMPLANTS

CROSS-REFERENCE TO RELATED APPLICATIONS

This application is a continuation application of U.S. patent application Ser. No. 15/203,843, filed on Jul. 7, 2016, which is a continuation application of U.S. patent application Ser. No. 14/964,613 filed on Dec. 10, 2015, (now issued as U.S. Pat. No. 9,408,651), which is a continuation application of U.S. patent application Ser. No. 14/701,577, filed May 1, 2015 (now issued as U.S. Pat. No. 9,237,917), which is a continuation of U.S. patent application Ser. No. 13/748,139, filed Jan. 23, 2013 (now issued as U.S. Pat. No. 9,232,971), which is a continuation of U.S. patent application Ser. No. 12/241, 979, filed Sep. 30, 2008, (now issued as U.S. Pat. No. 8,100,973), which is a continuation of U.S. patent application Ser. No. 11/105,783, filed Apr. 14, 2005, (now issued as U.S. Pat. No. 7,465,318), which claims priority to U.S. Provisional Application 60/562,686, filed Apr. 15, 2004 and U.S. Provisional Application 60/604,800, filed Aug. 24, 2004.

FIELD OF THE INVENTION

In general, the invention relates to orthopedic implants. More particularly, the invention relates to devices that are used to facilitate bone cement treatment of vertebral or other bone defects.

BACKGROUND OF THE INVENTION

There are many disease states and abnormal conditions that cause defects in the skeleton. For instance, osteoporosis and other metabolic bone conditions weaken the bone structure and predispose the bone to fracture. If not treated, certain fractures and bone defects may progress and lead to the development of severe neurological or other medical complications.

Other examples of bone defects are those resulting from the excision of benign or malignant lesions of the skeleton. Proliferation of tumors often compromises the structural integrity of the bone structure and thus requires surgical stabilization and filling of the defects with biological materials such as bone grafts or cements.

One approach to treating many bone defects comprises injecting, packing, or filling the defect with biocompatible bone cement. Such bone cements are generally formulations of non-resorbable biocompatible polymers such as PMMA (polymethylmethacrylate), or resorbable calcium phosphate or calcium sulphate cements, which allow for the gradual replacement of the cement with living bone. Both types of bone cements have been used successfully in the treatment of bone defects secondary to compression fractures of the distal radius, the calcaneous, the tibial plateau, and the vertebral body.

Historically, however, most applications of bone cements have been limited to open procedures in which the surgeon injects, packs, or tamps the biological material under direct visualization of the defect margins. Although direct visualization maximally allows the surgeon to identify adjacent structures that may be compromised by the inadvertent placement or injection of cement, less invasive means (apparatus and techniques) to assist the surgeon in safely and effectively placing biocompatible cements are generally desirable.

For example, one debilitating condition for which less invasive means to treat with injectable cement would be desirable is osteoporotic compression fracture of the spine. More than 700,000 osteoporotic compression fractures of the vertebrae occur each year in the United States—primarily in the elderly female population. Until recently, treatment of such fractures was limited to conservative, non-operative therapies such as bed rest, bracing, and medications.

A relatively new procedure known as "vertebroplasty" was developed in the mid 1980's to address the inadequacy of conservative treatment for vertebral body fracture. This procedure involves injecting radio-opaque bone cement directly into the fracture void through a minimally invasive cannula or needle under fluoroscopic control. The cement is pressurized by a syringe or similar plunger mechanism, thus causing the cement to fill the void and penetrate the interstices of broken trabecular bone. Once cured, the cement stabilizes the fracture and reduces pain usually dramatically and immediately.

One issue associated with vertebroplasty is containment of the cement within the margins of the defect. For instance, an osteoporotic compression fracture of the vertebral body may progress to an unstable intravertebral defect that is devoid of a cortical bone margin to contain the cement, and such a defect becomes an abnormal psuedo-joint that must be stabilized to progress to healing. Although the best alternative for treating such an intravertebral defect is the direct injection of bone cement into the defect to stabilize the vertebral body, there is a risk of cement flowing beyond the confines of the bone into the body cavity.

Yet another significant risk associated with vertebroplasty is the injection of cement directly into the venous system, since the veins within the vertebral body are larger than the tip of the needle used to inject the cement. A combination of injection pressure and inherent vascular pressure may cause unintended uptake of cement into the pulmonary vessel system, with potentially disastrous consequences including embolism to the lungs.

One technique which has gained popularity in recent years is a modified vertebroplasty technique in which a "balloon tamp" in inserted into the vertebral body via a cannula approach to expand or distract the fractured bone and create a void within the cancellous structure. Known tamps are inflated using pressurized fluid such as saline solution. The tamping effect, which may compact the cancellous vertebral bone to the extent it forms a barrier layer, is caused by the inflation of a balloon membrane that expands, thereby producing a radial force. When deflated and removed, the membrane leaves a void that is subsequently filled with bone cement. Creating a void within the cancellous bone by compacting the cancellous bone prior to injecting cement facilitates the use of larger filling cannulas and more viscous cement, which has been desirable because more viscous cement is less prone to unwanted or excessive cement flow.

There are, however, a number of limitations associated with such balloon tamp procedures. In particular, the balloon tamps currently known and used in the art may not produce sufficient forces to cause distraction. Partial healing of a chronic vertebral compression fracture places significant counterforce on the expanding membrane or container and limits the ability of the membrane or container to achieve full vertebral distraction, even while the patient is lying on the surgical table and the vertebral body is unloaded. Furthermore, as membranes are inflated with increasing pressure, radial forces are distributed equally and indiscriminately to all bone surfaces in contact with the membrane.

The membrane then preferentially expands within the bone in a direction offering the least counterforce. In the vertebral body, this direction is lateral in the transverse plane. Since it is generally desirable to correct deformity in the saggital plane, distractive forces delivered by conventional expanding membranes may often prove to be ineffective. As a result, a large void is created which destroys most of the remaining intact trabecular bone and which requires a large volume of cement for complete fill. Since toxicity and clinical complication rates increase with increasing volume of cement injected, this large volume may have deleterious clinical effects or may limit the extent of treatment to adjacent fractured levels.

Moreover, the long-term rate of success for treatment by injection of bone cement or other filler material can be increased by interdigitation of the cement or other filler material with the surrounding cancellous tissue, since interdigitation prevents relative movement of fractured bone fragments and thus relieves pain. Balloon tamps, however, are known to compact cancellous tissue—even to the point of forming what has been referred to as a "barrier layer"—which unfortunately retards such beneficial interdigitation. Poor cement/bone interface strength has lead to post operative dislodgement or loosening of the cement bolus, requiring medical and surgical intervention.

According to another recent method for treating bone defects such as vertebral fractures, a flexible mesh bag or container—which by itself, i.e., prior to filling, is non-load-bearing—is inserted into the void that has been formed in the bone and filled with cement, bone chips, or other filler material. Upon filling, expansion of the bag can also cause undesirable compaction of the surrounding cancellous bone. Moreover, depending on the porosity or permeability (or lack thereof) of the bag or container, the bag or container may, by itself, partially or completely preclude any interdigitation of the cement or filler material with the surrounding cancellous tissue.

Therefore, although the development of vertebroplasty, balloon-tamping, and container-based treatments represented an advance over prior, direct visualization techniques for treating bone defects, there remains a need for better means to repair and stabilize unstable intravertebral body defects (particularly those that have advanced to cortical wall defects) and other bone defects.

SUMMARY OF THE INVENTION

The present invention features a collapsible and self-restoring stent-type device used with bone cement or similar filler material (referred to generically herein as bone cement) to treat bone defects, particularly within the vertebral body. The device includes a collapsible, self-restoring wire lattice or braided primary structure and flow-directing features.

The primary structure serves to maintain patency of the cavity in which the device is inserted while the bone cement is being injected; it is in that sense that the device is like a stent. (In this regard, a stent or stent-type device may be defined as a structure having sufficient strength in radial compression to maintain the separation of two or more tissue surfaces surrounding a void within a bone defect or fracture, e.g., to maintain manually or otherwise generated separation or distraction of the vertebral endplates during bone cement-based treatment of vertebral fractures.) However, unlike balloons, bags, or other container-type devices that have been used previously to generate and/or maintain separation or distraction, the primary structure of the invention does so without compacting cancellous bone or forming a barrier layer around the cavity. Thus, the cancellous bone at the margins of the bone cavity has relatively normal trabecular architecture, and that fosters beneficial interdigitation of bone cement with the surrounding cancellous bone.

The flow-directing features of the device, on the other hand, control the direction and rate of bone cement flow when cement is injected into the cavity so as to avoid unwanted cement flow beyond the cortical bone margins or into vascular sinuses or neural structures, all of which can cause clinical complications. Various flow-directing features are contemplated, including (but not limited to) baffles attached to the primary structure, holes or slots selectively formed in the primary structure, and differential porosity of various regions of the primary structure. Possible baffling elements may include co-braided filaments which occupy the spaces of the metal lattice or braid of the primary structure without altering the formability or elasticity of the overall structure, or they may include non-woven secondary films or coatings which adhere to regions of the lattice without altering the formability or elasticity of the structure. Overall, however, the device creates minimal total flow resistance or backpressure and thus directs, rather than contains, cement

BRIEF DESCRIPTION OF THE DRAWINGS

These and other features and advantages of the invention will become clearer from the description below and the figures, in which.

DETAILED DESCRIPTION

Figure 1:
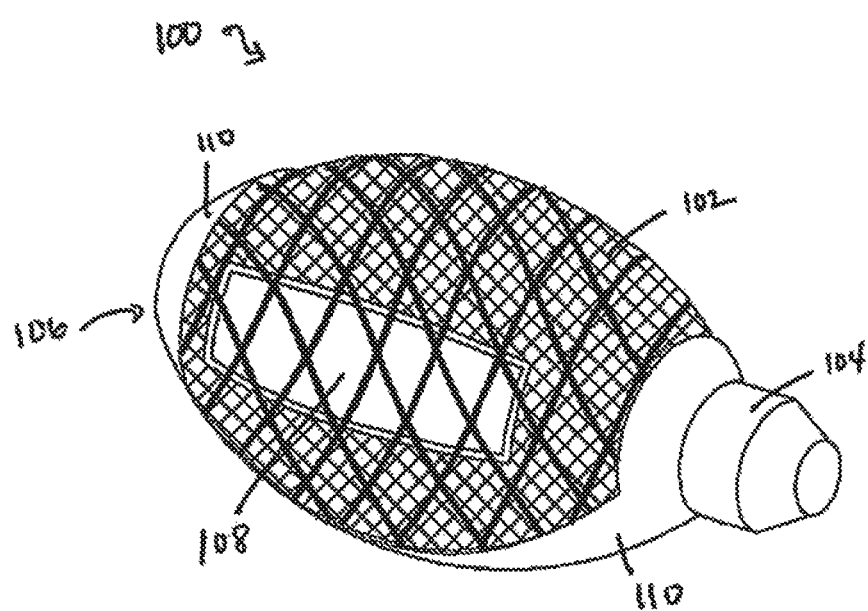
FIGS. 1-4 are a perspective view, a top view, a side elevation view, and an end view, respectively, of one embodiment of a cement-directing device according to the invention.

A first embodiment 100 of a cement-directing structure according to the invention is illustrated in FIGS. 1-11. As illustrated, the hollow structure 100 may be generally ovoid or football-shaped in form (although various other shapes are also contemplated as falling within the scope of the invention, as noted below). In general, the structure 100 features an elastic, self-restoring core member 102 that is crimped, welded, glued, sewn shut, or otherwise closed on one end 104 and open or non-crimped at the opposite end 106; one or more cement flow windows 108 (the illustrated embodiment having a pair of cement flow windows 108); and a flow-retarding baffle member 110. As will be explained in greater detail below, the cement flow windows 108 and the baffle member 110 provide regions of differential cement flow permeability as compared to the surrounding regions of the core member 102, and that differential permeability enables the structure 100 according to the invention to control the direction in which cement flows when being injected into a cavity formed within a bone. Although the embodiment 100 utilizes both cement flow windows 108 and a baffle member 110, it is contemplated that cement-directing structures according to the invention will work satisfactorily if either only cement flow window(s) or only baffle member(s) is or are used.

The core member 102 is formed from a multiplicity of elastic, heat-setting monofilament wire members (e.g., Nitinol wires) that are braided together in a plain braid fashion to form a collapsible, self-expanding, generally tubular structure using techniques that are known in the art. Other metallic or polymeric monofilament wires may also be used. The shape-memory /shape-restoring properties of alloys (particularly Nitinol), however, make them preferred. The core member 102 has sufficient mechanical strength and elasticity to assume its nominal shape upon complete insertion into a bone cavity and to contact opposed fractured surfaces, thereby providing some support to the surfaces and maintaining patency of the cavity.

Figure 5:
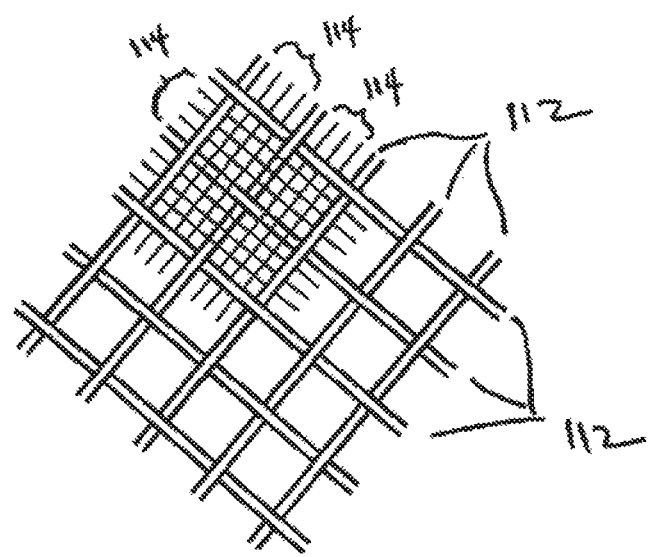
FIGS. 5-8 are detail views illustrating possible braid configurations used in the device shown in FIGS. 1-4.
Figure 6:
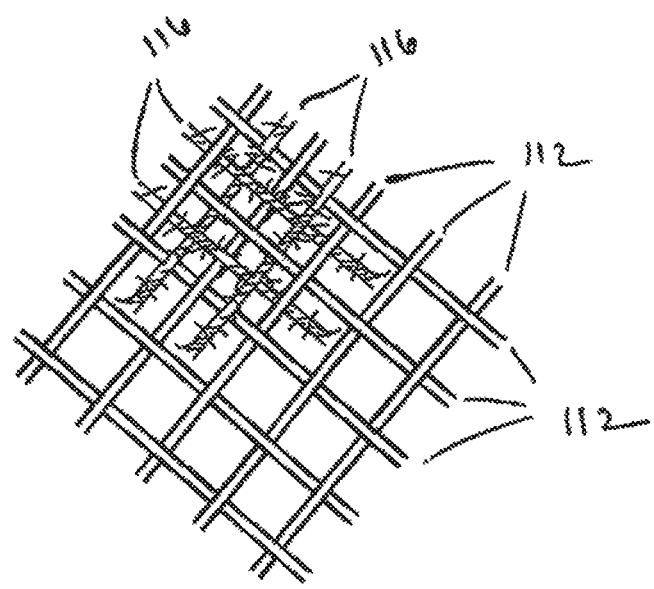
Figure 7:
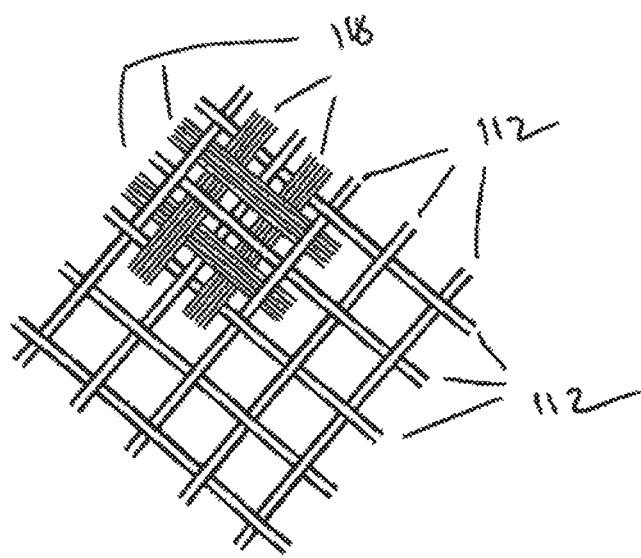
Figure 8:
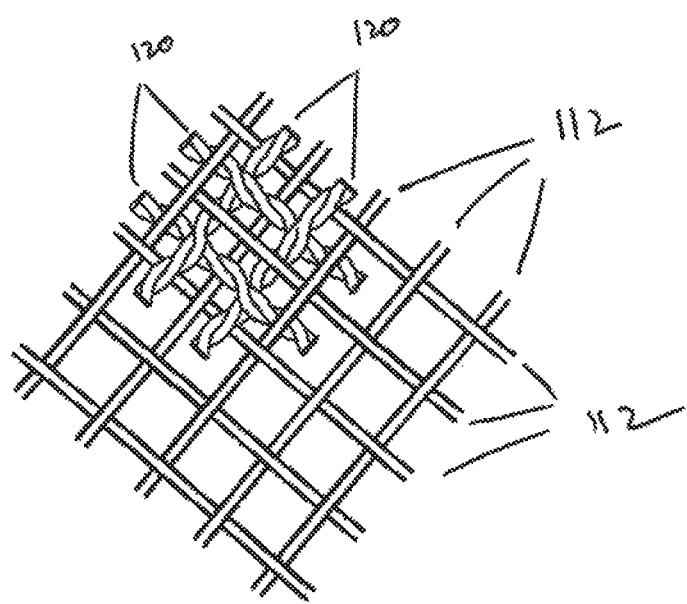

As illustrated in FIGS. 5-8, the preferred embodiment is actually a co-braided structure having primary wire members 112 with secondary members interwoven therewith. The secondary members may be smaller and more elastic than the primary wire members 112, which are the members that are the primary source of the structure 100's shape and self-restoring capability. By way of non-limiting example, as illustrated in FIG. 5, the secondary members 114 may be monofilament metal wires that are finer than the primary wire members 112; as illustrated in FIG. 6, the secondary members 116 may be frayed polymeric multifilament yarns; as illustrated in FIG. 7, the secondary members 118 may be flat wire or flat braid; or as illustrated in FIG. 8, the secondary members 120 may be stranded multifilament wire. The type and properties of the secondary members (e.g., number of wires, braid angles, diameters, etc.) will be selected to achieve a desired overall combination of properties such as stiffness, strength, mesh density, etc.

The cement flow windows 108 are regions of the core structure 102 where the secondary members have been removed from the meshwork formed by the primary wire members 112, thus leaving areas of increased permeability to cement flow relative to the surrounding regions of the core structure 102. The rest of the surface of the structure, however, remains co-braided. Thus, cement will tend to flow preferentially out of the cement flow windows 108 when it is injected into the interior of the cement-directing structure 100. The secondary members may be removed from the structure of the core member 102 by laser or mechanical cutting after the core member has been formed and heat-set in its desired configuration.

Figure 4:
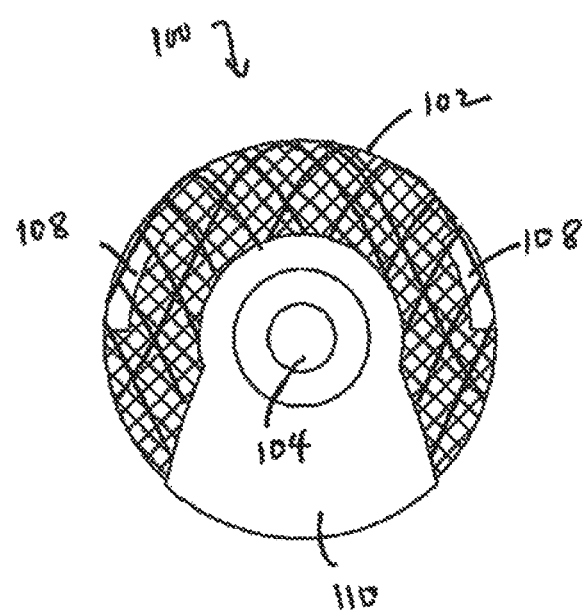

The specific location of the cement flow window(s) 108 will, of course, depend on clinical intent. According to a presently preferred configuration, however, two cement flow windows 108 are provided. Lengthwise speaking, as best illustrated in FIG. 1 (only one cement flow window 108 being visible therein), the cement flow windows 108 are approximately centered between the two ends 104 and 106 of the cement-directing structure 100, and the length of each window 108 is between approximately 50% and approximately 75% of the overall length of the structures. Circumferentially speaking, as best illustrated in FIG. 4, each cement flow window 108 subtends approximately 30° of arc, and the two cement flow windows 108 are located approximately 120° to approximately 160° apart from each other (center to center), symmetrically located above and below the lateral midplane 109 of the structure 102.

The baffle 110, on the other hand, provides a region or regions of decreased permeability to cement flow as compared to the surrounding regions of the core structure 102. In other words, the baffle 110 blocks or severely restricts the flow of cement out of cement-directing structure 102 in specific locations when cement is injected into the interior of the structure 102. In this regard, the baffle 110 may be formed as an impermeable, flexible polymeric sheet or coating that is attached or bonded to either the inside or the outside of the core braided structure 102. The flexible polymeric coating may be silicone or other biocompatible materials such as EPTFE (expanded polytetroflouroethylene) or polyurethane, or it may comprise a tightly woven fabric such as polyester or other biocompatible or degradable suture material. The coating may be attached or adhered to the structure by a number of manufacturing processes known in the art, such as dip coating or electrospinning. The approximate thickness of the baffle coating is 0.0005 to 0.003 inches, so the coating will not preclude elastic deformation of the overall braided structure.

Figure 2:
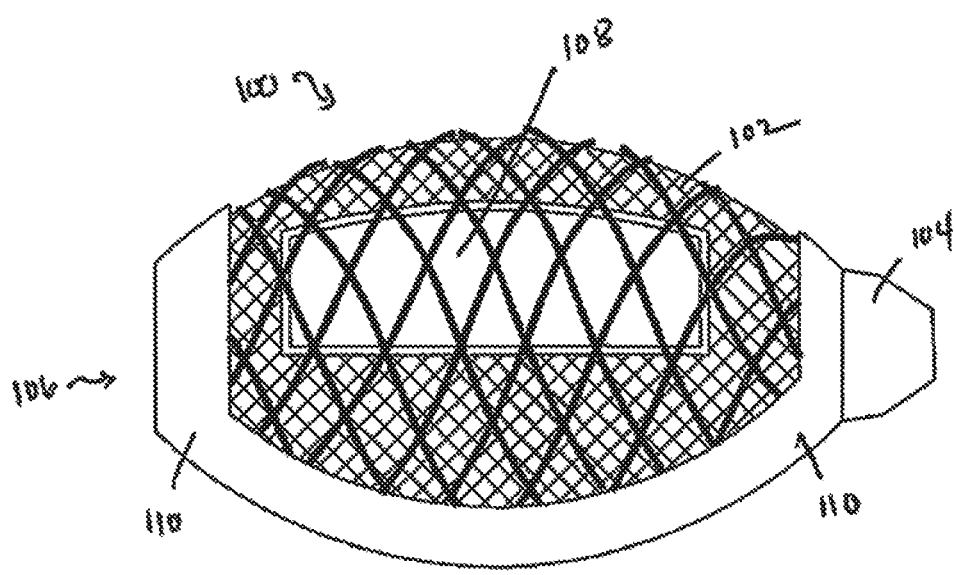
Figure 3:
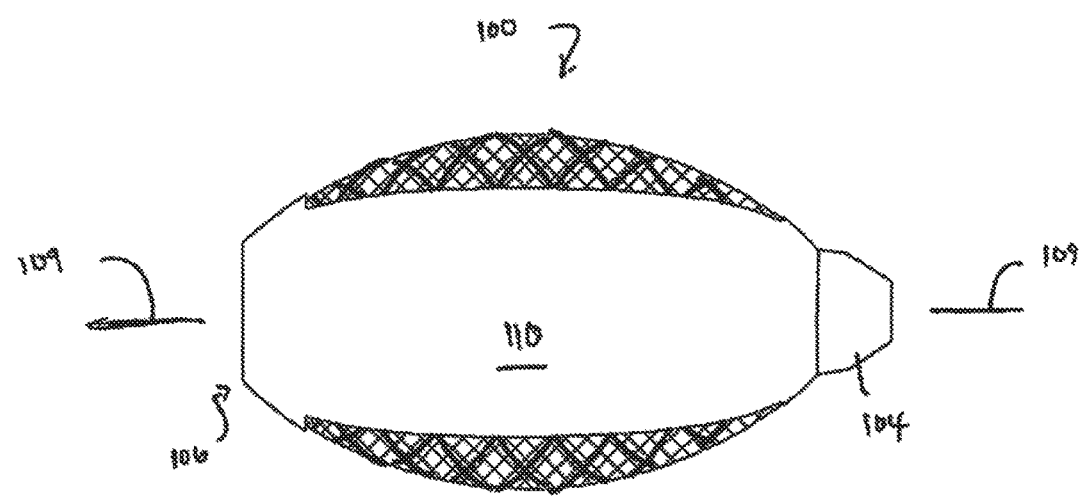

As is the case with respect to the cement window(s) 108, the precise location of the baffle 110 will depend on clinical intent. According to the presently preferred embodiment, however, the baffle 110 extends all the way from one end 104 of the device to the opposite end 106 and covers the ends, as illustrated in FIGS. 1-3. Circumferentially speaking, the baffle 110 subtends an arc of approximately 60° to approximately 80°, centered on and extending above and below the lateral midplane 109 of the structure 102.

Figure 9:
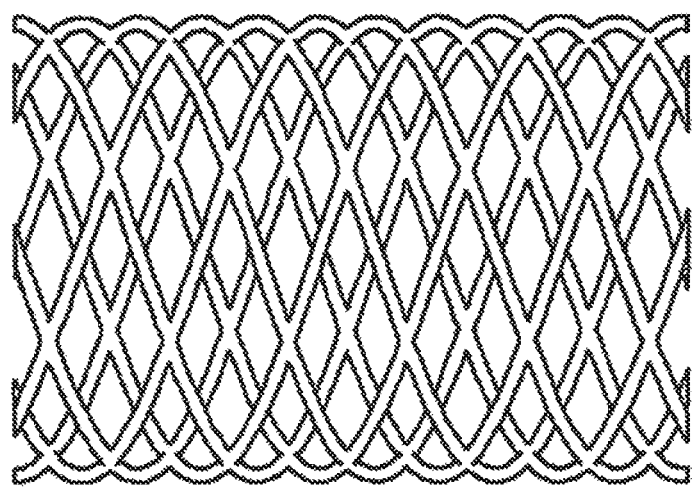
FIGS. 9-11 illustrate intermediate steps in the construction of a device as shown in FIGS. 1-4.
Figure 10:
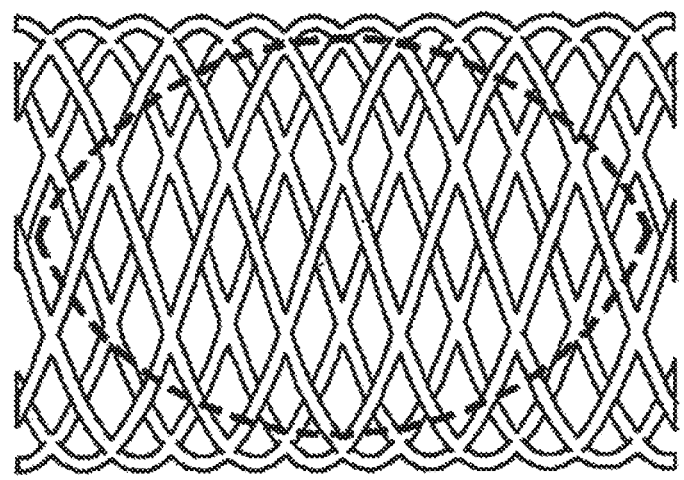
Figure 11:
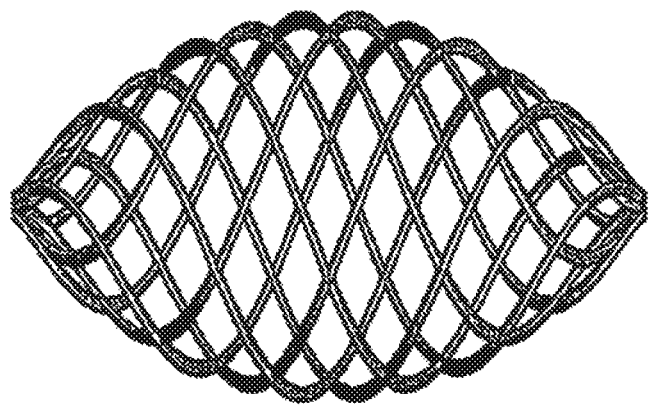
Figure 12:
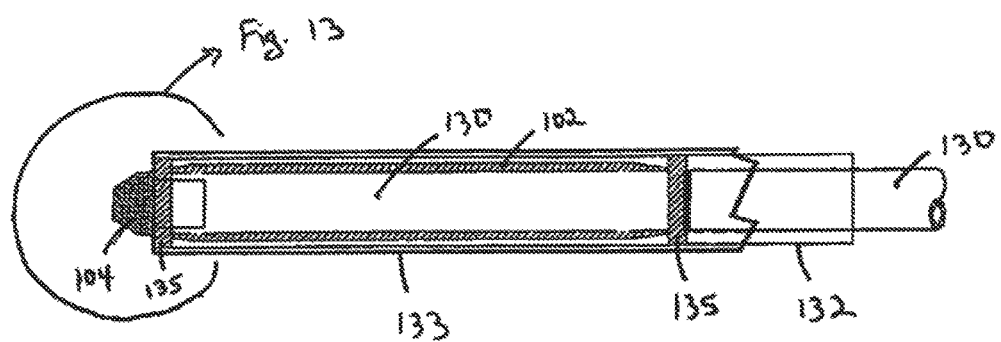
FIGS. 12-16 are sequential side views illustrating a device according to the invention loaded in and then being ejected from a cannula for insertion into a bone cavity.
Figure 13:
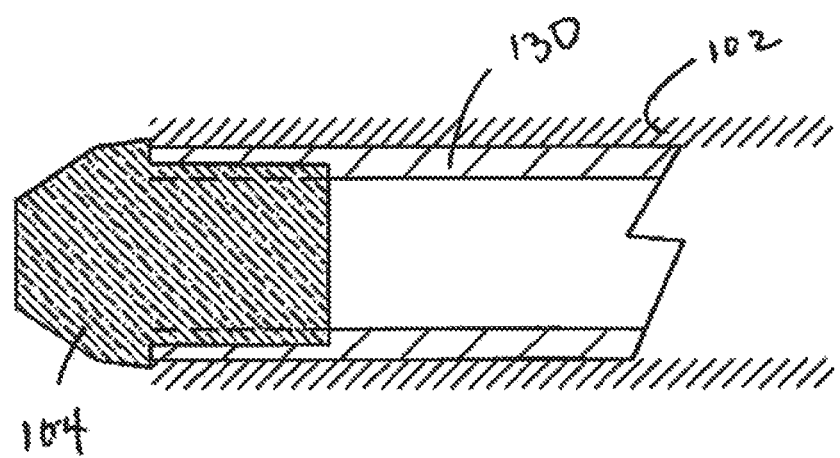
Figure 14:
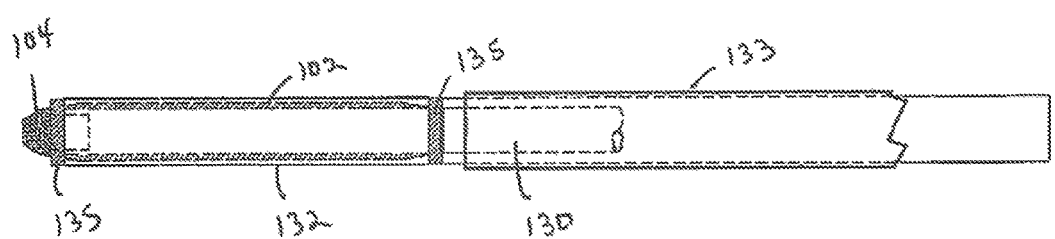

Basic construction of a structure 100 according to the invention is illustrated in FIGS. 9-11. First, a hollow tubular structure like that shown in FIG. 9 is formed on a braiding machine, as is known in the art. The structure will include the primary wire members 112 and any secondary members (not shown in FIG. 9). The wires are then annealed sufficiently to maintain a specific diameter and to prevent the wires from unraveling when the braided tube is cut to a specific length. As illustrated in FIG. 10, the cut, braided tube is then placed over a mandrel (shown in phantom) having the desired shape of the final product and collapsed down onto the mandrel, and further heat set into the final desired shape as illustrated in FIG. 11 (secondary members not shown). The mandrel is then removed by opening the wires on one end of the structure, at which end the ends of the wire are left free or ungathered in order to facilitate collapsibility of the structure for insertion into a delivery catheter. The other end of the structure (e.g., the end 104 in FIGS. 1-3) is then gathered and preferably crimped with a metal tube or sewn shut. If a metal crimp is used, it may be made from radioopaque material (e.g. high-density metal such as platinum or tantalum) to facilitate location of the structure 100 within the vertebral body by means of fluoroscopy. (In addition to the crimp tube, at least some of the secondary members of the braid may also be made from radioopaque material such as platinum, or some of the wires of the structure 102 (either primary or secondary) may be coated with radioopaque ink as known in the art.) The cement flow windows 108 are then formed by selectively removing secondary members as described above, and the baffle 110 is formed, e.g., by coating the primary or core structure 102 as also described above.

Insertion and cement-directing operation of a structure 100 within a vertebral body VB is illustrated in FIGS. 12-20. In particular, the delivery device used to insert the structure 100 is illustrated in FIGS. 12-16, and the structure is illustrated in place and directing the flow of cement within the vertebral body in FIGS. 17-20.

As illustrated in FIGS. 12-16, since the structure 100 has one closed end 104 and one open end 106, it is preferred to collapse the structure 102 over a hollow push rod 130 prior to inserting the structure 100 into a catheter sheath 132, so that the push rod is effectively linked to the closed end 104 of the structure 102. (The catheter sheath may, itself, include radioopaque marker bands 135, as is known in the art.) The hollow push rod 130 facilitates placement of the collapsed, enclosed structure into the cavity, via a cannula 133, through its removable connection to the closed end of the structure. The removable connection may be a mechanical linkage, such as a thread or luer lock, or other suitable attachment.

Figure 15:
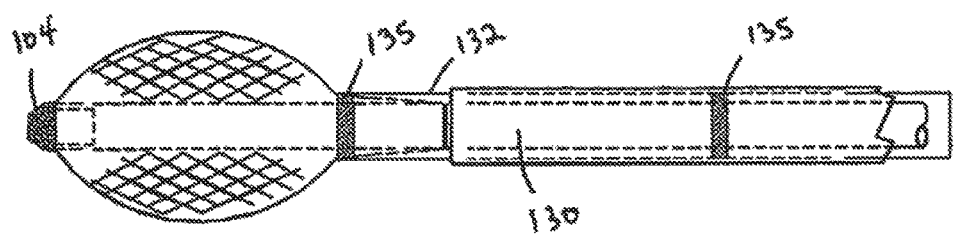
Figure 16:
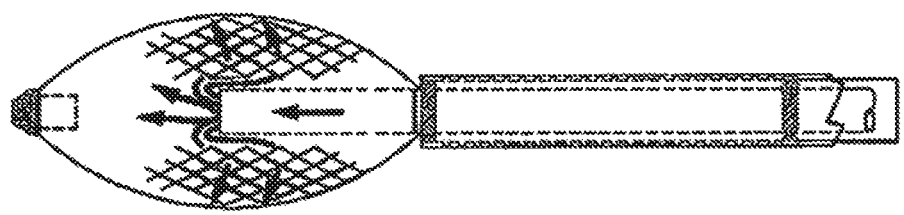
Figure 17:
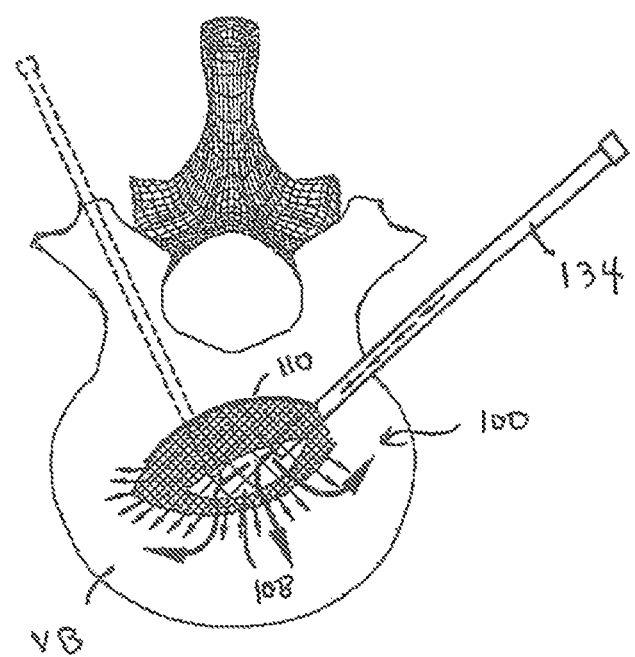
FIGS. 17-20 are views in the transverse plane and in the saggital plane of the vertebral body, illustrating the flow of cement into and through a device according to the invention and the resultant location of hardened cement masses obtained thereby.
Figure 18:
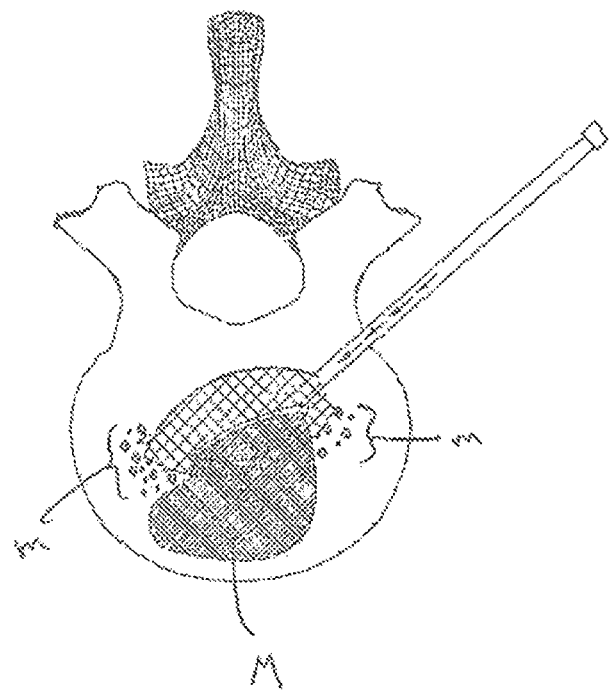
Figure 19:
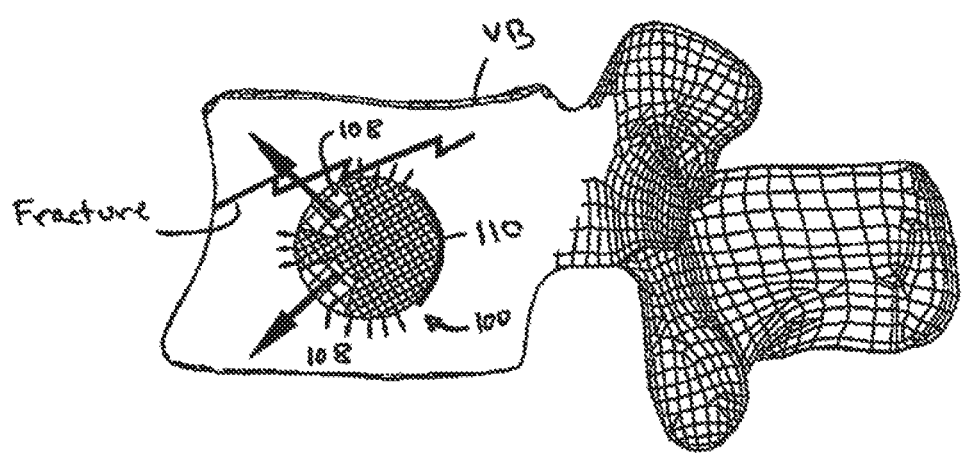
Figure 20:
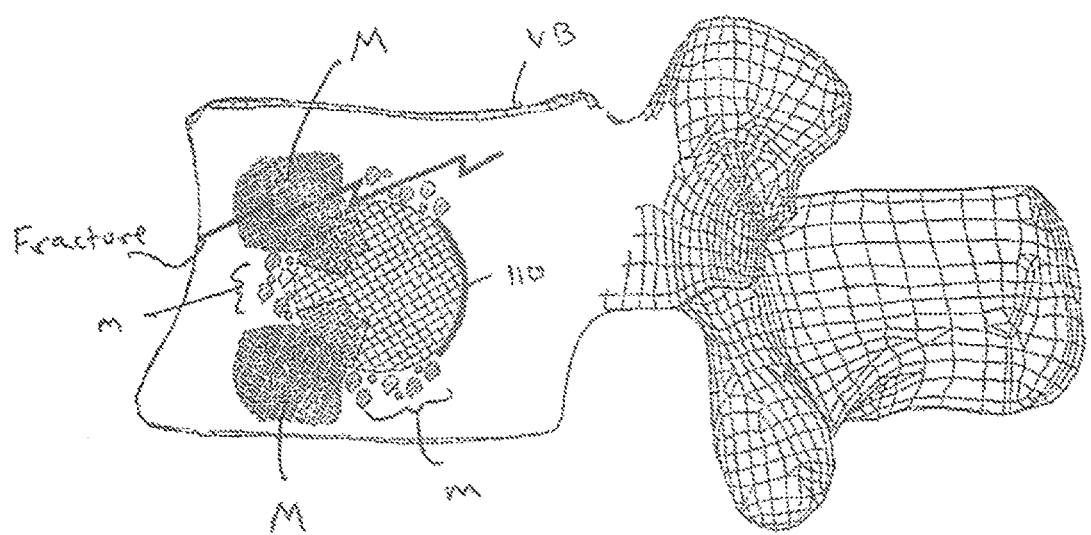

Once the sheath-covered structure 102 is fully inserted into the cavity formed within the bone structure being treated, the sheath 132 is retracted, as illustrated in FIG. 15 and the self-restoring structure expands to its final shape, as illustrated in FIGS. 15 and 16. The removable connection between the closed end 104 of the structure 102 and the push rod 130 is severed, and the hollow push rod 132 is partially retracted until its tip is located generally in the center of the structure 102, at which point the push rod may be used secondarily as a cement injector.

A filling portal (not shown) on the other end of the rod is then connected to a cement injection syringe via a luer lock fitting (not shown). Cement can then be injected into the center of the structure, as indicated by directional arrows shown in the cannula 134. It is preferable that the open end of the structure be collapsed around the hollow push rod 132, thereby forming a slideable connection that assures lengthwise positioning and targeting of the flow portal of the push rod 132 within the center axis of the self-restoring device and easy removal of the push rod after filling with cement.

(Alternatively, a separate filling needle (shown in phantom in FIG. 17) capable of penetrating the structure 102 could perforate the meshwork or baffle of the structure after deployment of the structure in the bone cavity, so that the cement injection is not restricted to any particular vector; indeed, the structure 102 may be filled in multiple orientations at multiple points of entry. By perforating the outer mesh, the needle flow portal may be placed in the center of the device or, if necessary, entirely through the device to regions of the bone external to the device where it may be desirable to inject cement directly into a bone fracture site.)

As illustrated in FIGS. 17-20, the regions of differential permeability—viz. the cement flow windows 108 and the baffle 110—effectively control the direction of flow of cement into the vertebral body into which the structure 100 is inserted.

In particular, a greater amount of cement will flow out of the cement flow windows 108, as represented by the relatively thick, large arrows, than will flow out of the remainder of the structure 100, as represented by the relatively thin, small arrows. For the given orientation of the structure 100 within the vertebral body, with the cement flow windows 108 facing anterior-superior and anterior-inferior and the baffle 100 facing posterior, significant masses M of cement will be directed anterior-superior and anterior-inferior into the forward third of the vertebral body, thereby forming "mantles" of cement which cross the plane of the vertebral fracture. The cement "mantles" will be located adjacent to the vertebral endplates and thus will form a load-bearing column of cement.

Where other flow of cement out of the structure 100 exists, smaller volumes or masses m of cement will form. These smaller masses m of cement will beneficially interdigitate with the surrounding healthy bone tissue, thereby helping to anchor the structure of the invention in place within the vertebral body VB.

Conversely, the baffle 110, which is impermeable to cement, will block the flow of cement out of the structure 100 in the posterior direction. Advantageously, this helps prevent cement from flowing posteriorly, e.g., into the posterior venous complex, spinal canal, etc.

Figure 21:
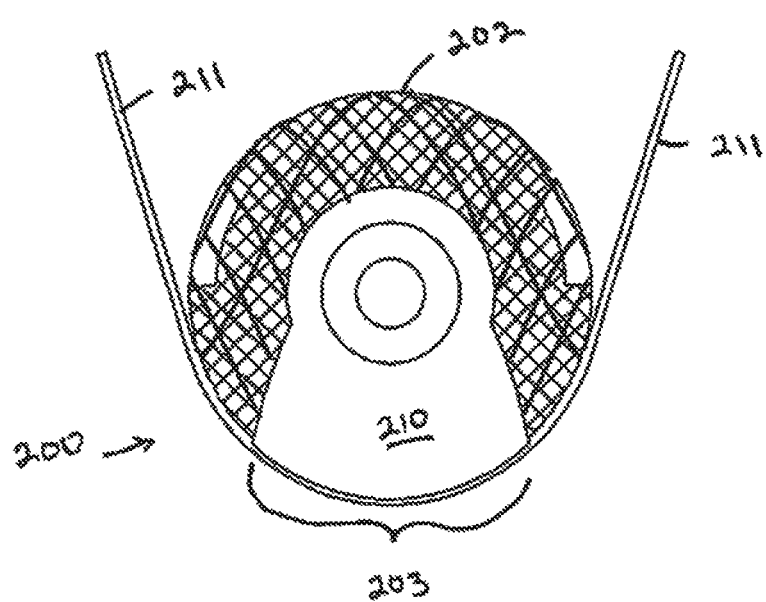
FIGS. 21 and 22 are an end view and a side elevation view of an alternate embodiment of a cement-directing structure according to the invention.
Figure 22:
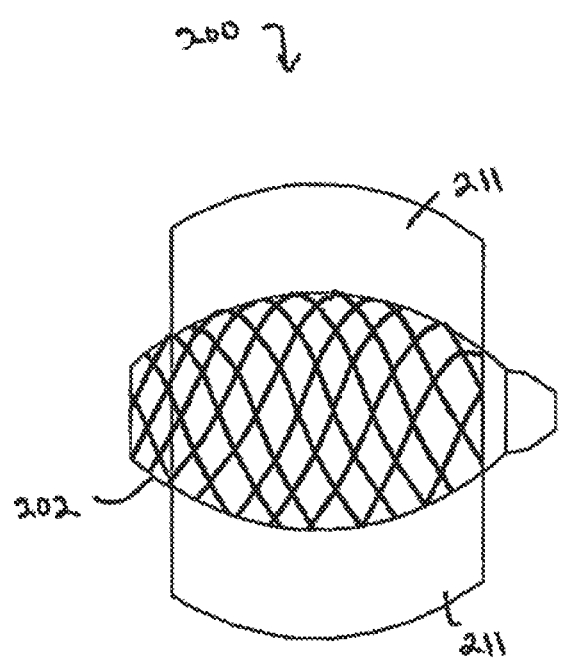

A modified embodiment 200 of a cement-directing structure according to the invention is illustrated in FIGS. 21 and 22. In this embodiment, the baffle 210 further includes a flexible, sheet-like material 211 formed from either solid polymer film, non-woven polymer film, or woven fabric that is connected to the primary braided structure 202 along a single region 203 and that extends from the primary braided structure so that the flexible sheet-like material 211 may be wrapped around the structure 202 without being adhered to the structure. The sheet-like structure 211 is therefore unconstrained and may open independently of the self-restoring structure 202. This embodiment 200 allows cement to flow freely through the structure 202 and contact the sheet-like baffle structure 211. The force of cement contact will cause the sheet-like baffle 211 to open to the limits defined by the bone cavity, or until an equilibrium between forces of flowing cement with the resistive force of the bone cavity is attained.

Figure 23:
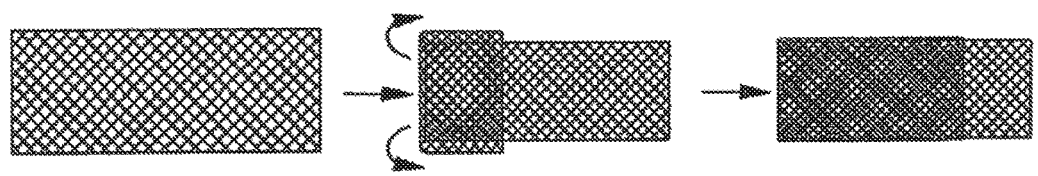
FIG. 23 is a sequence of side elevation views illustrating the manufacture of an alternate embodiment of a cement-directing device according to the invention.

Other variations in the invention are also possible. For example, using a variant of the manufacturing method described above, a multi-layered braided structure can be formed. For example, it is known that braids can be formed in multiple layers over a mandrel. Alternatively, the original braided tube structure may be folded back on itself prior to heat-setting, as illustrated in FIG. 23, to create a double-layered or multiple-layered braided structure. Double- or multi-layering of the braided structure increases stiffness of the structure and can assist in directing the flow of cement by increasing the mesh density where layers of the structure overlap.

Figure 24:
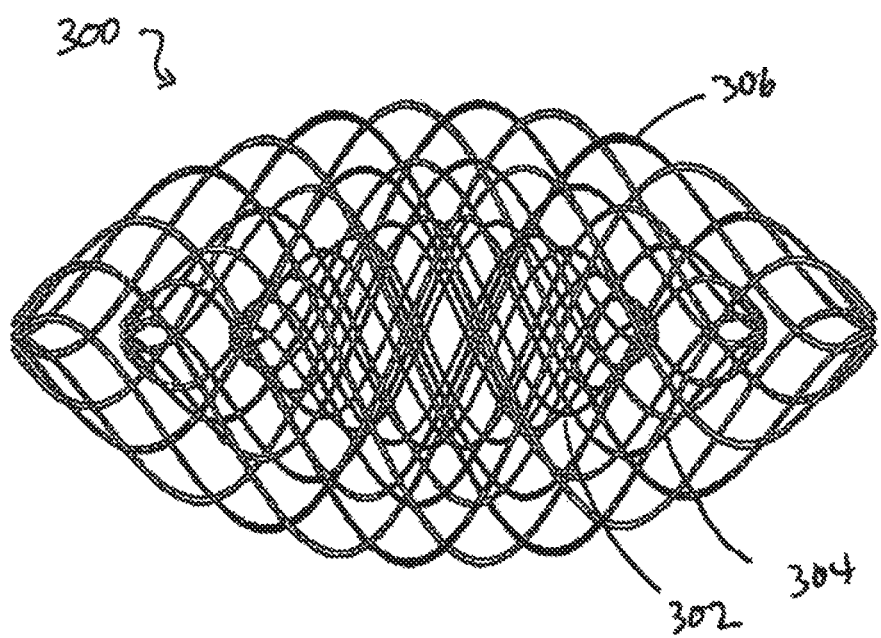
FIG. 24 is a side view of another alternate embodiment of a cement-directing device according to the invention.

Another multi-layered variation 300 of a cement-directing structure according to the invention is shown in FIG. 24, wherein two additional layers 302, 304 of elastic braided filament are nested within the outermost layer 306. These sequential layers could be formed over a mandrel (not shown) then heat-set together. The multiple layers may all be collapsed into a tubular form (not shown) while nested together before being slidingly fit into a sheath.

If the stacked, multi-layer structure is too thick to fit in a sheath in the collapsed state for deployment, then a layered structure may be constructed in vivo by deploying individual self-restoring structures sequentially into the original expanded structure. In that specific instance, the outer layer 306 would have an opening sufficient to accept the second layer 304 such that when assembled in vivo the second layer occupies the opening of the first layer. The inner expandable structures 302, 304 may or may not have a baffling component, supplementary filaments, or coatings, yet would provide enhanced mechanical strength as each layer expands and contacts the outer layer. Each consecutive device would be pre-assembled in the collapsed state into a cannula and then deployed through the cannula in sequence (not shown). The plurality of layers defined in this alternate embodiment has the secondary benefit of reinforcement to the cement mantle.

Figure 25:
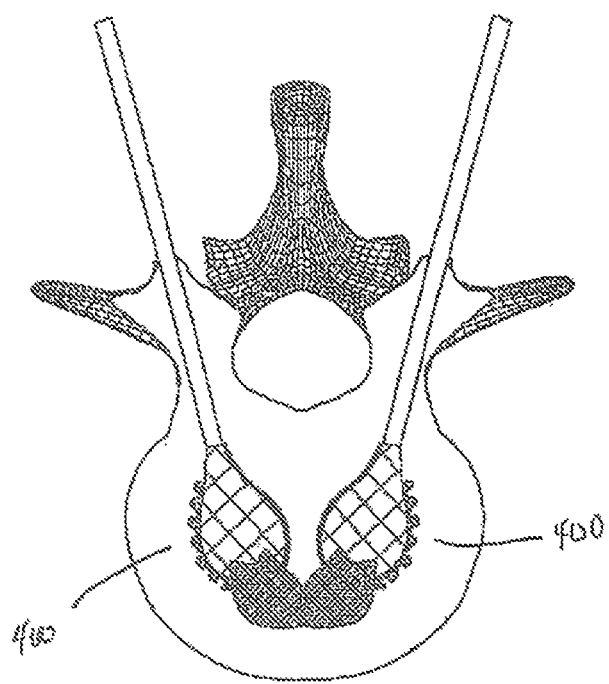
FIGS. 25 and 26 are views in the transverse plane and in the saggital plane in the vertebral body illustrating an alternate embodiment of a cement-directing device according to the invention.
Figure 26:
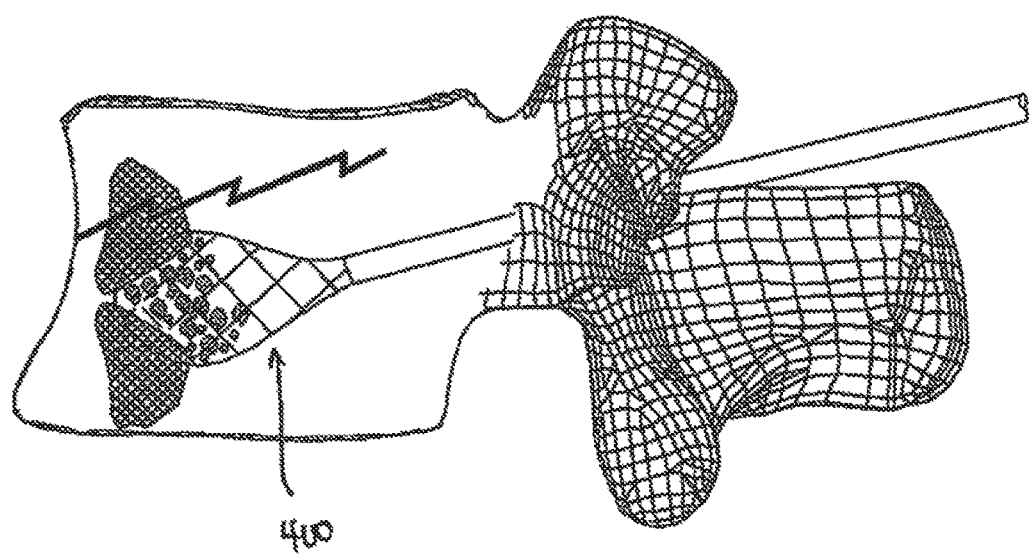
Figure 27:
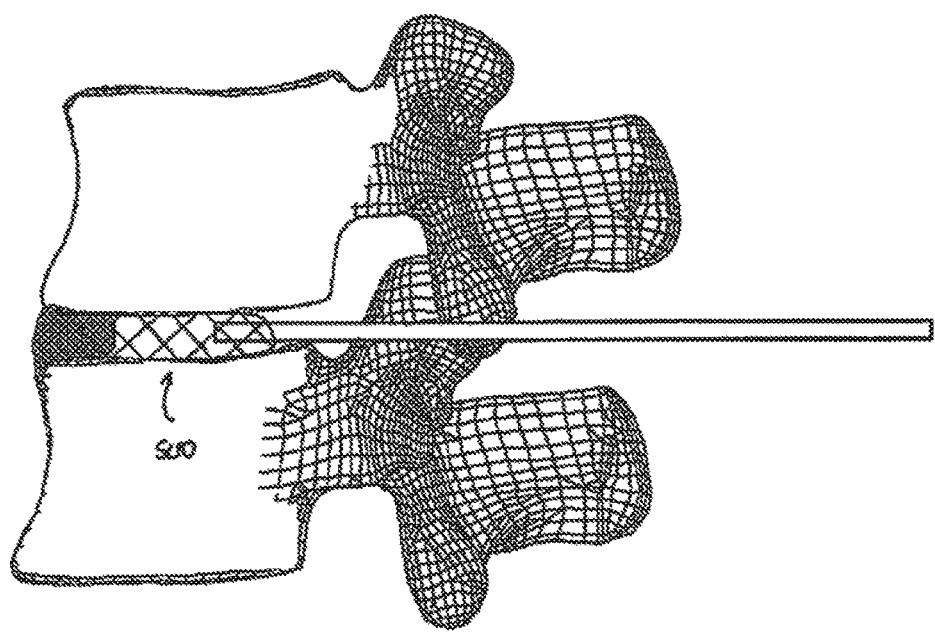
FIG. 27 is a view in the saggital plane of a pair of vertebral bodies illustrating an alternate embodiment of a cement-directing device according to the invention being used for spinal fusion following discectomy.

In addition to these variant embodiments, shapes other than the ovoid or football shape shown in the Figures above may be desirable. For example, oblong or pear-shaped cement-directing structures 400 might be desired where, for example, when it is clinically indicated to approach the vertebral body bilaterally, through each pedicle, as illustrated in FIGS. 25 and 26. Alternatively, a relatively thin cement-directing structure 500 might be employed for spinal fusion techniques, as illustrated in FIG. 27, wherein the cement-directing structure is deployed through minimally invasive means into the disc space to provide support to the spinal column following discectomy. Finally, although a mesh structure formed by braiding has been disclosed and described above, those having skill in the art will appreciate that self-expanding, collapsible mesh structures can be formed by a variety of other techniques, e.g., laser-cutting tubes, etc, and the invention is not limited to braided mesh structures.

These and other variations to the embodiments disclosed and described above will occur to those having skill in the art. To the extent such variations incorporate the inventive concepts disclosed herein, they are deemed to fall within the scope of the following claims.

What is claimed is:

1. A device for use in treating orthopedic defects in a procedure, said device comprising:
   a collapsible, expandable mesh structure configured to have a first, collapsed configuration and a second, expanded configuration,
   wherein said mesh structure comprises co-braided primary members and secondary members occupying interstices between said primary members, and
   wherein said mesh structure has regions of different permeability or flow resistance configured to control the direction of bone cement or other orthopedic filler material through said mesh structure.

2. The device of claim 1, wherein said mesh structure is elastic and capable of self-expansion.

3. The device of claim 1, wherein said mesh structure includes a coating on at least a portion of said mesh structure.

4. The device of claim 3, wherein the coating defines a flow-retarding baffle member.

5. The device of claim 4, wherein the flow-retarding baffle is formed on select regions of said mesh structure.

6. The device of claim 1, wherein the primary and secondary members comprise wire members.

7. The device of claim 1, wherein the primary and secondary members are different from one another.

8. The device of claim 1, wherein the secondary members are smaller than the primary members.

9. The device of claim 1, wherein the first, collapsed configuration is maintained by a sheath.

10. The device of claim 1, wherein said mesh structure has at least one region in which the mesh opening size of said region is greater than the mesh opening size of surrounding regions.

11. The device of claim 10, wherein said mesh structure is configured such that bone cement flows preferentially out of the device through said at least one region of greater mesh opening size.

12. The device of claim 1, wherein said device is generally hollow and has first and second ends, both of which are closed.

13. The device of claim 1, wherein said device is generally hollow and has first and second ends, said first end is fastener closed and said second end is unrestrained.

14. A device for use in treating orthopedic defects in a procedure comprising inserting the device into a cavity within a bony member and injecting bone cement or other orthopedic filler material into an interior region of the device, said device comprising:
   a flexible mesh structure configured to move between a collapsed position and an expanded position, wherein the flexible mesh structure has sufficient rigidity to maintain walls of the cavity apart from each other in the expanded position;
   wherein the mesh structure is a co-braided structure including primary members and secondary members occupying interstices between said primary members.

15. The device of claim 14, wherein said mesh structure has regions of different permeability or flow resistance.

16. The device of claim 14, wherein said structure includes a coating on a portion of outer surface of the mesh structure to control the direction of the bone cement or other orthopedic filler material through the mesh structure.

17. The device of claim 14, wherein the mesh structure is elastic and capable of self-expanding.

18. The device of claim 17, wherein the secondary members are smaller than the primary members.

19. The device of claim 14, wherein the primary and secondary members are wire and are different from one another.

20. The device of claim 14, wherein the first, collapsed configuration is maintained by a sheath.

* * * * *